(12) United States Patent
Sengupta et al.

(10) Patent No.: US 7,632,292 B2
(45) Date of Patent: Dec. 15, 2009

(54) ASSEMBLY FOR THE STABILISATION OF VERTEBRAL BODIES OF THE SPINE

(76) Inventors: Dilip Kumar Sengupta, 101 Delaunays Road, Crumpsall, Manchester (GB) M8 4RE; Robert Charles Mulholland, 39 Private Road, Sherwood, Nottingham (GB) NG5 4DD (*) Notice: Subject to any disclaimer, the term of this patent is extended or adjusted under 35 U.S.C. 154(b) by 661 days.

(21) Appl. No.: 10/480,986

(22) PCT Filed: Jun. 17, 2002

(86) PCT No.: PCT/GB02/02709

§ 371 (c)(1),
(2), (4) Date: Jun. 6, 2005

(87) PCT Pub. No.: WO02/102259

PCT Pub. Date: Dec. 27, 2002

(65) Prior Publication Data

US 2006/0240533 A1 Oct. 26, 2006

(30) Foreign Application Priority Data

Jun. 16, 2001 (GB) ................................ 0114783.4

(51) Int. Cl.
*A61B 17/70* (2006.01)
(52) U.S. Cl. ...................................... 606/257; 606/254
(58) Field of Classification Search ................... 606/61, 606/254, 255, 257, 263; 623/17.13; 267/70, 267/167, 178, 179, 160, 161, 164
See application file for complete search history.

(56) References Cited

U.S. PATENT DOCUMENTS

| | | | | | |
|---|---|---|---|---|---|
| 3,261,244 | A | * | 7/1966 | Smoyak et al. | 81/417 |
| 3,271,847 | A | * | 9/1966 | Millheiser | 29/229 |
| 4,743,260 | A | | 5/1988 | Burton | |
| 5,415,611 | A | * | 5/1995 | Krayenhagen | 492/16 |
| 5,415,661 | A | * | 5/1995 | Holmes | 606/255 |
| 5,645,599 | A | * | 7/1997 | Samani | 623/17.16 |
| 6,267,764 | B1 | * | 7/2001 | Elberg | 606/255 |
| 6,572,653 | B1 | * | 6/2003 | Simonson | 623/17.13 |

FOREIGN PATENT DOCUMENTS

| | | |
|---|---|---|
| FR | 2 735 351 | 12/1996 |
| FR | 2 799 949 | 4/2001 |
| WO | WO 98/22033 * | 5/1998 |

* cited by examiner

*Primary Examiner*—Eduardo C Robert
*Assistant Examiner*—Elana B Fisher

(57) ABSTRACT

An assembly for the stabilisation of vertebral bodies (12, 14) of the spine is described. It comprises a pair of pedicle screws (20) each having a threaded shaft (20a) with a tapering first end (20b) for introduction into a vertebral body and a head portion (20c) with a second end (20d), and is characterised in that it further comprises a spring member (18, 22, 24, 40, 42, 44) of the following form. The spring member has first and second ends, substantially straight portions (18b) adjacent each end and a substantially curvilinear central portion (18a) therebetween, the straight portions and the substantially curvilinear central portion being substantially coplanar. The assembly also includes a pair of fixation mechanisms (26) for securing the first and second ends of the spring member to the pair of pedicle screws. Typically the assembly will be for stabilisation of two adjacent vertebral bodies of the spine, that is one motion segment.

23 Claims, 4 Drawing Sheets

ASSEMBLY FOR THE STABILISATION OF VERTEBRAL BODIES OF THE SPINE

The invention relates to an assembly for the stabilisation of vertebral bodies of the spine of the kind which is secured to the adjacent vertebral bodies by pedicle screws, and in particular although not exclusively to such an assembly for stabilisation of two adjacent vertebral bodies.

The lumbo-sacral region of the human spine consists of five lumbar vertebrae located above the large triangular bone called the sacrum. Between adjacent lumbar vertebrae are inter-vertebral discs (IVD) which have a complex structure, with a central jelly like nucleus pulposus and a peripheral rim of tough fibrous layers, the annulus fibrosus. Each lumbar vertebra is made up of a vertebral body, with upper and lower end plates, which contact the IVD's, and facet joints located posteriorlly. Movement in the lumbo-sacral spine occurs in the IVD's at the front and at the facet joints at the rear. Thus, the IVD's and the facet joints provide stability of the motion segment between adjacent vertebra. However, they also transfer load from one vertebra to the next, and it is estimated that the IVD bears approximately 80% of the load and the pair of facet joints at the rear bear approximately 20% of the load. A normal IVD can distribute the load uniformly across the surface of the end plate of the vertebral body. However, when the IVD and/or the facet joints are damaged or degenerate this can lead to instability of the motion segment between adjacent vertebra and commonly to low back pain. It is considered that the pain can be caused by abnormal movement, and/or by abnormal distribution of load across the end plates of the vertebrae.

Conventional treatment of low back pain is to limit movement between adjacent vertebrae, typically by fusing the adjacent vertebrae together. However, fusion has a high failure rate of pain relief.

More recently treatment with prosthetic IVD's has been tried in an attempt to preserve the normal movement and normal load bearing of the inter-vertebral joints. However, thus far the results are no better than in fusion of adjacent vertebrae.

An alternative approach is that of "soft stabilisation" which aims to prevent abnormal motion in painful motion segments of the lumbo-sacral spine, but to save as much as possible of the normal motion. Several methods of soft stabilisation have been described in the literature, but only two are currently in use.

The Graf ligament system consists of a fabric ligament secured across pedicle screws located in the adjacent vertebrae. Typically two such ligaments are located across each motion segment, one to each side on the rear of the spine. This system creates lordosis (curvature of the spine, convex forwards) and restricts the movement of the motion segment between the vertebrae concerned, but it also increases the load at the posterior part of the IVD. In one such system (Dynesys-Sulzer, as described in European patent application published under No. EP 0 669 109) excessive lordosis is prevented by a cylinder embracing the ligament between the pedicle screws. However, actual distraction of the disc space can only be achieved by producing flexion of the motion segment. This results in a kyphotic (convex backwards) segment, and kyphotic segments in the lumbo-sacral spine can produce back pain. Hence, there are significant problems with the use of such a system.

The other soft stabilisation system which is in the process of development is a fulcrum assisted soft stabilisation system (FASS) which is described in International patent application No. PCT/CH99/00612. In this system the compressing effect of the ligament found in the Graf ligament system is converted into a distraction effect by the use of a fulcrum bridging between the pedicle screws, and located between the ligament and the spine. This system can unload the IVD in forward flexion but not in extension. However, it is known from the literature that the IVD is loaded both in flexion and extension and the facet joints are specifically loaded in extension. Hence, this system also is expected to suffer from disadvantages.

None of the available soft stabilisation systems therefore addresses the important aim of addressing uniform IVD distraction to create a normal loading pattern across the end plates of the vertebrae, both in flexion and extension.

It is an aim of the present invention to provide a new soft stabilisation system which addresses that aim, and mitigates the problems described above.

According to the present invention there is provided an assembly for the stabilisation of vertebral bodies of the spine comprising a pair of pedicle screws each having a threaded shaft with a tapering first end for introduction into a vertebral body and a head portion with a second end, characterised in that it further comprises:

a spring member having first and second ends, substantially straight portions adjacent each end and a substantially curvilinear central portion therebetween, the straight portions and the substantially curvilinear central portion being substantially coplanar; and a pair of fixation mechanisms for securing the first and second ends of the spring member to the pair of pedicle screws.

The substantially curvilinear central portion of the spring member may be C-shaped or a coil.

The substantially curvilinear central portion of the spring member typically has a radius of curvature in the range 3 to 17 mm or in the range 5 to 15 mm.

The substantially straight portions of the spring member may be at an angle to each other in the range 0 to 180 degrees, or 90 to 180 degrees. When the straight portions are at 180 degrees they are substantially coaxial. When the substantially straight portions of the spring member are at 0 degrees they are parallel, and this is most likely when the central curvilinear portion is a coil.

Preferably the spring member is formed from wire.

The spring member may have a diameter in the range 1 to 6 mm, or in the range 2 to 5 mm.

The spring member may have substantially straight portions of greater cross sectional area than that of the substantially curvilinear portion.

The assembly may have a pair of sleeves, one on each of the substantially straight portions, to effectively increase the external diameter of at least a part of each of the substantially straight portions.

Such sleeves may have external diameters in the range 5 mm to 8 mm.

The spring member may be round in cross section, or alternatively may be square or rectangular in cross section. The spring member is preferably formed from titanium or stainless steel.

The threaded shaft portions of the pedicle screws may have lengths in the range 30 to 60 mm, or in the range 35 to 55 mm. Preferably the pedicle screws are formed from titanium.

The assembly may be for stabilisation of two adjacent vertebral bodies of the spine, i.e. one motion segment. Typically for such embodiments the spring member has a length in the range 20 to 65 mm, but it may be in the range 25 to 60 mm.

The assembly may have a spring member which is specifically adapted for stabilisation of three vertebral bodies of the spine, that is two motion segments.

In such embodiments, the spring member typically has a length in the range 50-110 mm, but it may be in the range 60-100 mm.

Embodiments of the invention will now be described, by way of example only, with reference to the accompanying drawings in which.

Figure 1:
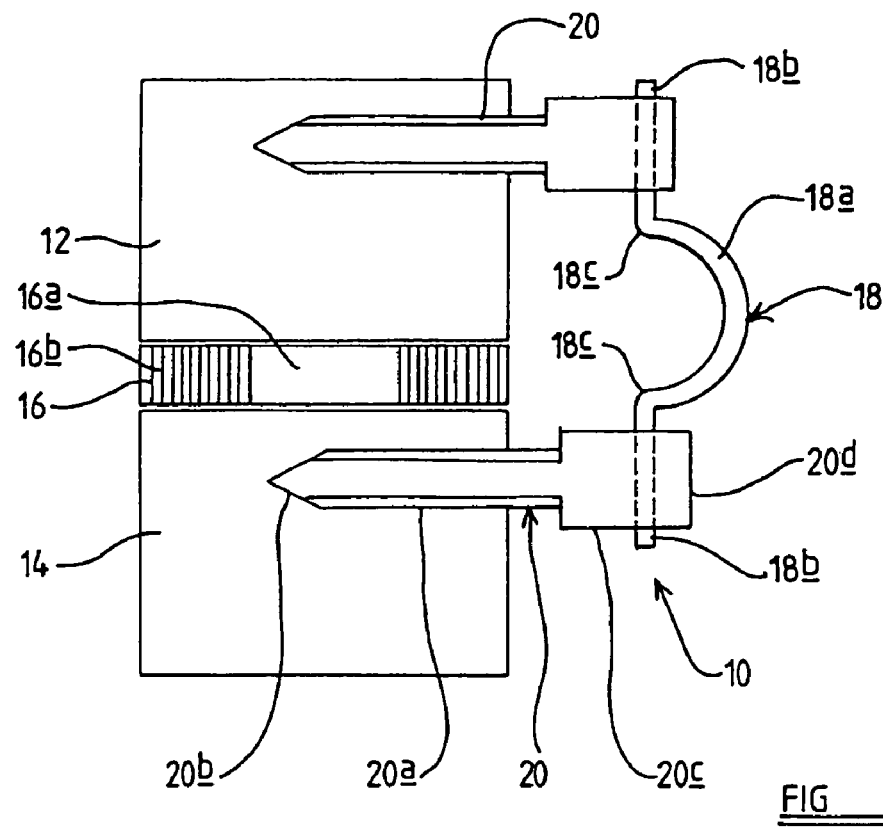
FIG. 1 is a schematic illustration of an assembly according to the invention in use.
Figure 3:
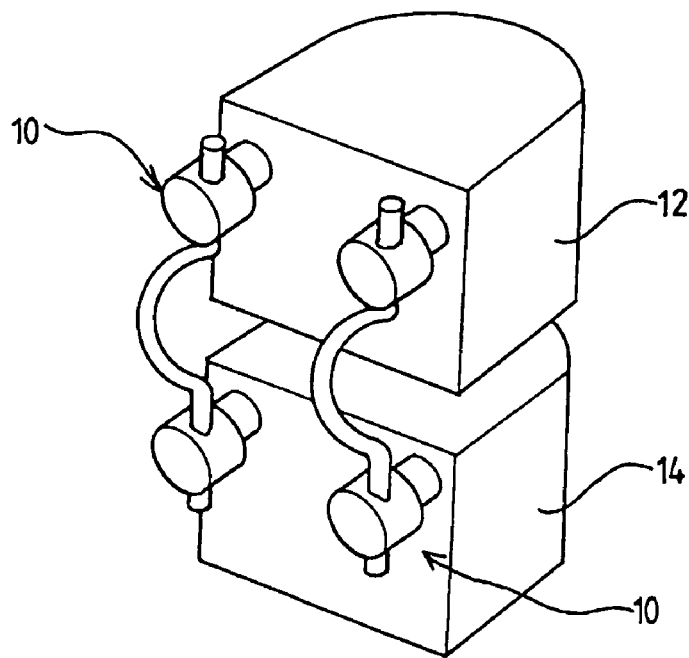
Figure 4A:
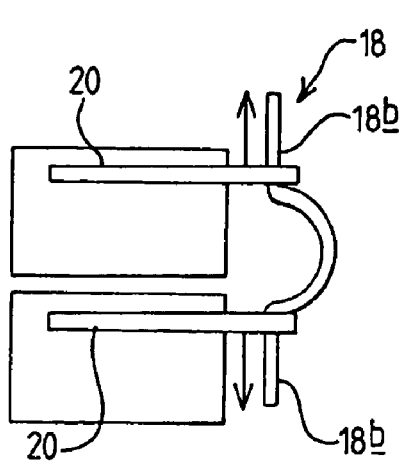
Figure 4B:
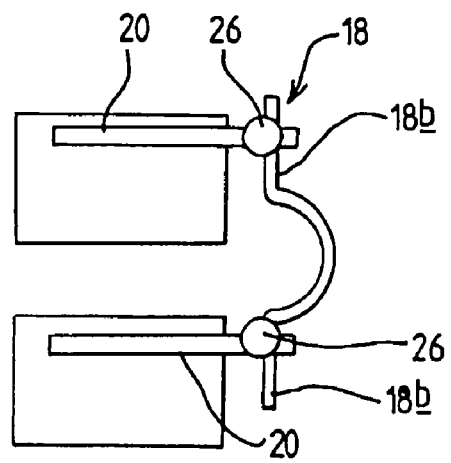
Figure 5A:
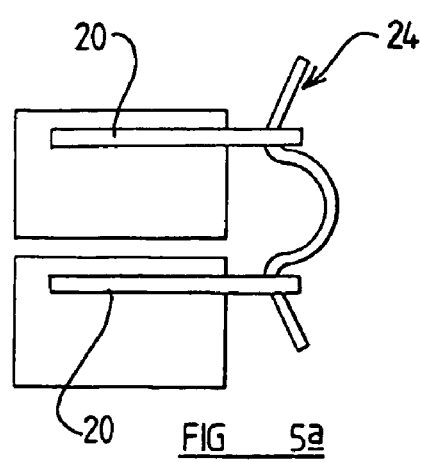
Figure 5B:
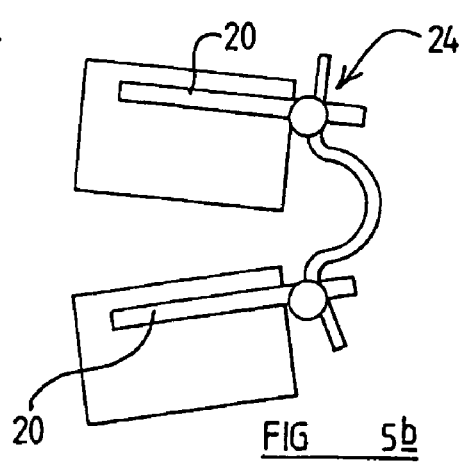
Figure 6A:
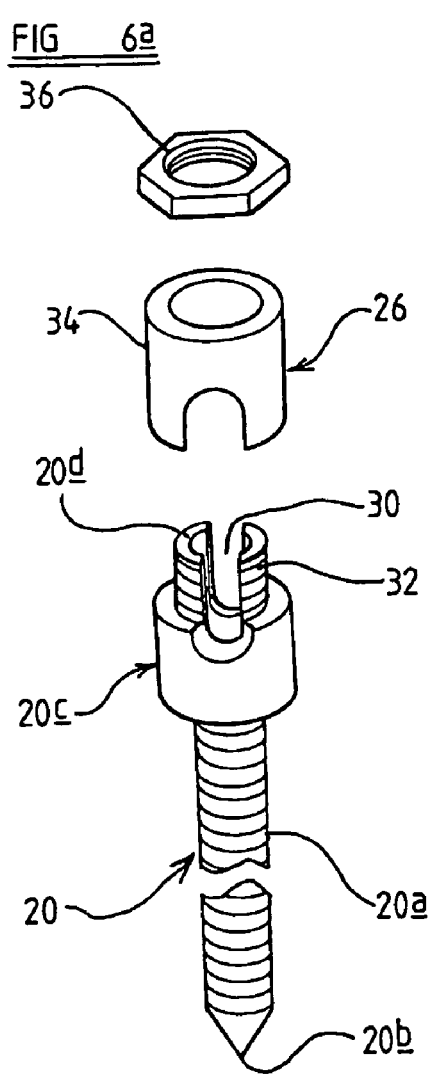
Figure 6B:
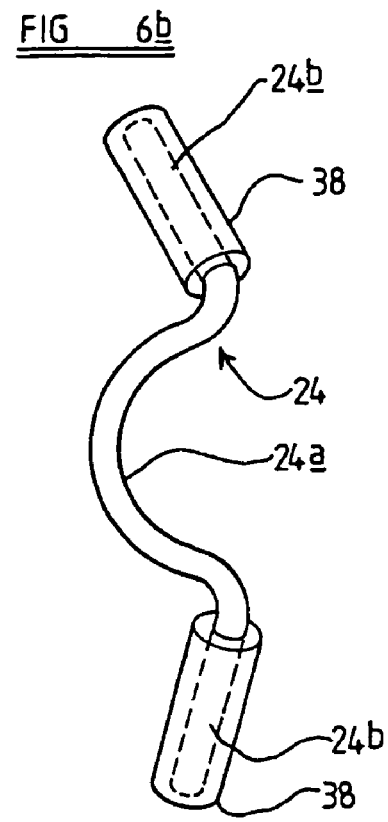
Figure 7A:
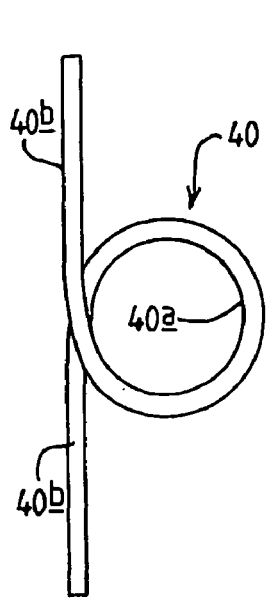
Figure 7B:
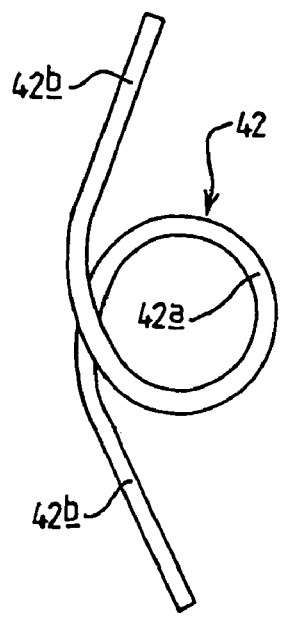
Figure 7C:
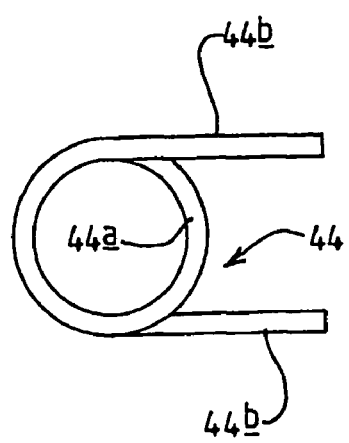
Figure 8:
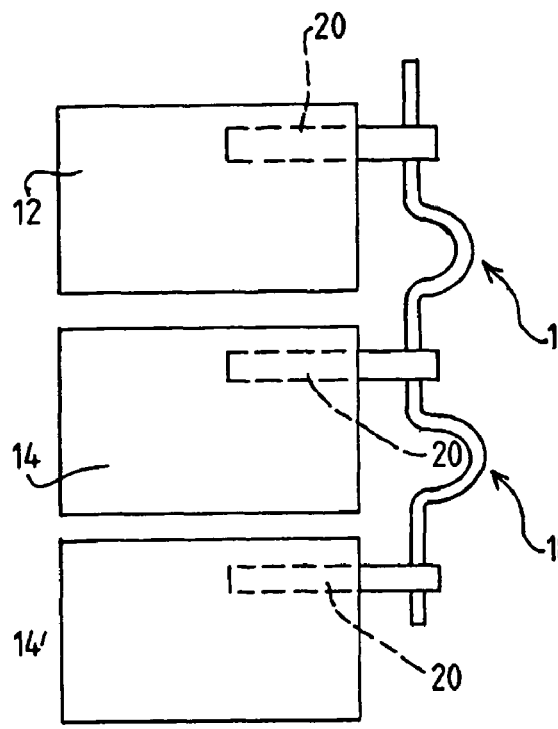
Figure 9:
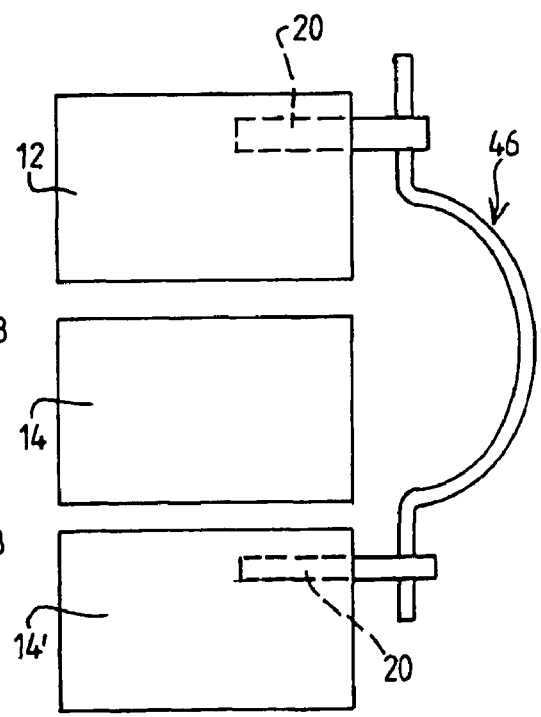

FIG. 3 schematically illustrates a pair of assemblies according to the invention in use, from perspective angle;

FIGS. 4a-4b illustrate schematically how the assembly of FIG. 1 can be used for distraction of the motion segment;

FIGS. 5a-5b illustrate schematically how the assembly according to the invention can be used to cause backward angulation of the motion segment;

FIGS. 6a-6b illustrate a fixation mechanism suitable for use in the assembly of FIG. 1;

FIGS. 7a-7c illustrate three further alternative spring members;

FIG. 8 illustrates schematically two assemblies according to the invention used across adjacent motion segments, and FIG. 9 illustrates schematically an alternative embodiment of an assembly according to the invention for use across two motion segments.

Referring first to FIG. 1, an assembly 10 for the stabilisation of two adjacent vertebral bodies 12, 14 of the spine is illustrated schematically. The vertebral bodies 12, 14 are separated by an inter-vertebral disc 16 which has a nucleus pulposus 16a and a fibrous outer-annulus, called the annulus fibrosus, 16b. For simplicity the facet joints have been omitted from the posterior of the vertebral bodies 12, 14. For clarity the assembly 10 is fixed to the posterior of the vertebral bodies 12, 14.

The assembly 10 comprises a spring member 18 which has a central substantially curvilinear portion 18a, which in this embodiment is C-shaped, and substantially straight portions 18b extending outward therefrom. The straight portions 18b and curvilinear portion 18a are joined by reverse curvature portions 18c.

The assembly 10 further comprises a pair of pedicle screws 20 each of which comprises a threaded shaft portion 20a with a tapering first end 20b and a head portion 20c with a second end 20d.

The assembly 10 is illustrated in position secured to the posterior of a pair of adjacent vertebral bodies 12, 14 with the threaded shaft portions 20a of the pedicle screws 20 inserted into the vertebral bodes 12, 14. The spring member 18 is secured to the heads 20c of each of the pedical screws 20 by a fixation mechanism as appropriate. An example of a fixation mechanism will be described later, although any appropriate mechanism may be used.

Figure 2A:
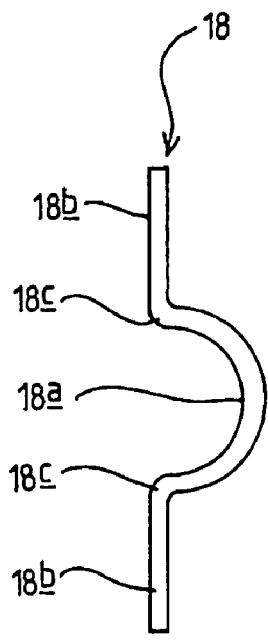
FIGS. 2a-2c illustrate three alternative embodiments of a spring member. for incorporation in the assembly of FIG. 1.

Referring now in particular to FIG. 2, three examples of spring members for incorporation into an assembly according to the invention are illustrated. FIG. 2a shows the spring member 18 from FIG. 1. In the spring member 18 the substantially straight portions 18b are coaxial, i.e. at an angle of 180° to each other, and the substantially curvilinear portion 18a is C-shaped and approximately a semi-circle. The reverse curvature portions 18c are of small radius and approximate to right angles.

Figure 2B:
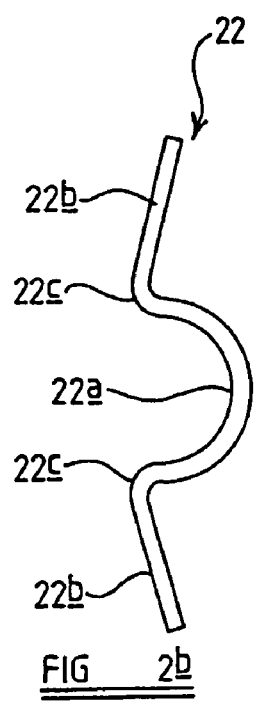

In FIG. 2b a first alternative spring member 22 is illustrated in which the substantially straight portions 22b are at an angle to each other of approximately 150°, and the substantially curvilinear portion 22a is again C-shaped and approximately a semi-circle. The substantially straight portions 22b and the substantially curvilinear portion 22a are joined by reverse curvature portions 22c which in this spring member 22 are of relatively small radius, but not as small as in the embodiment above.

Figure 2C:
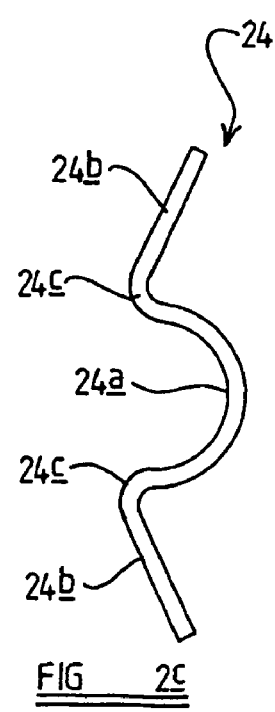

In FIG. 2c a third embodiment of a spring member 24 is illustrated. The spring member 24 again comprises two substantially straight portions 24b with a substantially curvilinear portion 24a therebetween, these portions being joined by reverse curvature portions 24c which are of a larger radius of curvature than those 22c in the previous embodiment. The substantially straight portions 24b are again at an angle to each other, this time of approximately 140°.

The substantially curvilinear portions 18a, 22a, and 24a are all shown as being smooth curves approximating to a semi-circle. However, they could take other forms, such as for examples being smaller arcs of a circle, or indeed not being strictly curvilinear but comprising a plurality of short straight portions.

The substantially straight portions 18b, 22b and 24b, are all shown as being straight, but they could in alternative embodiments be very slightly curved. They will generally be at angles to each other in the range 90 to 180° for embodiments such as these with C-shaped curvilinear central portions 18a, 22a and 24a.

In each of the spring members 18, 22 and 24 the substantially straight portions and the substantially curvilinear portion are coplanar.

The spring members 18, 22 and 24 are made from titanium or stainless steel wire, each spring member being bent from a single piece. The wire will typically have a diameter in the range 1 to 6 mm, but preferably in a range of 2 to 5 mm. The wire may be round in cross-section or may be of other forms e.g. square, rectangular, or oval in cross section.

The spring members 18, 22 and 24, which are all designed to be used between adjacent vertebral bodies, have an overall length in the range 20 mm to 65 mm, but preferably in the range 25 mm to 60 mm.

Referring now in particular to FIG. 3, a pair of assemblies 10 according to this invention are shown secured to a pair of adjacent vertebral bodies 12, 14. This is the manner in which the assembly 10 will generally be used, with one assembly 10 applied to either side of the vertebral bodies on the posterior aspect of the spine.

Referring now to FIGS. 4 and 5, two effects of use of the assemblies 10 are seen illustrated. In FIG. 4, it can be seen that unloading of the inter-vertebral disc can be achieved by separation of the pedicle screws 20, or distraction of them, along the substantially straight portions 18b of the spring member 18 before securing the spring member 18 to the pedicle screws 20 using the fixation mechanisms 26. Thus the assembly 10 will hold the vertebral bodies 12, 14 further apart, unloading the disc, yet still permit some movement which is relatively normal.

In FIG. 5 the use of an alternative embodiment of spring member 24, in which the substantially straight portions 24b are at an angle to each other, can be seen providing backward angulation (lordosis) of the motion segment between the adjacent vertebral bodies which in some conditions will be desirable.

Referring now to FIG. 6 an example of a fixation mechanism 26 is illustrated, the mechanism being known in the prior art. The head 20c of the pedicle screw 20 is shown with a particular form. It comprises a slot 30 which provides the dual purpose of accepting the blade of a screw driver for insertion of the pedicle screw 20 into a vertebral body, and for receipt of the substantially straight portions 24b of the spring member 24. The head 20c further comprises adjacent its second end 20d, and around the upper part of the slot 30, a threaded portion 32.

The fixation mechanism 26 further comprises a sleeve member 34 and threaded nut 36, also sleeves 38 which are located on the substantially straight portions 24b of the spring member 24 before the assembly 10 is put together as shown in FIG. 6b. The sleeves 38 effectively increase the outer diameter of the spring member 24 as necessary for use in the fixation mechanism 26. For example, for a spring member 24 formed from wire with a diameter of 3 mm or 4 mm the sleeves 38 may typically increase the diameter to somewhere in the range 5 mm to 8 mm, as appropriate for the pedicle screw being used. As an alternative, the substantially straight portions 24b of the spring member 24 may be formed with a greater diameter than that of the substantially curvilinear portion 24a, and thus have a greater cross-sectional area than the substantially curvilinear portion 24a.

Figure 6C:
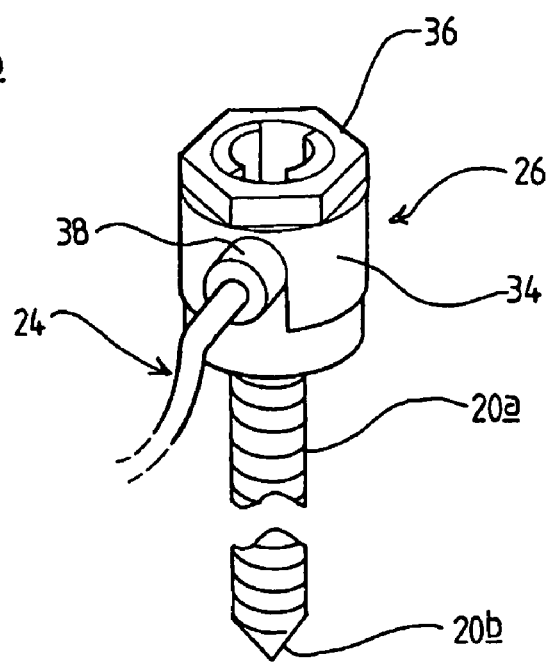

The fixation mechanism 26 is shown assembled in FIG. 6c. Once the screw 20 has been inserted into the vertebral body one substantially straight portion 24b of the spring member 24, with sleeve 38 in place, is located in the slot 30. The sleeve member 34 is then placed over the head 20c of the pedicle screw 20, and the nut 36 screwed down onto the threaded portion 32 to retain the spring member 24 in place. The fixation mechanism 26 may further include a check nut (not shown), as is known in the prior art, to further secure the mechanism together and to reduce the possibility of it loosening over time.

It should be appreciated that the fixation mechanism 26 is one example of many options which would be available, and any appropriate fixation mechanism may be used.

Referring now to FIG. 7 three further embodiments of spring members according to the invention are illustrated. In the first, as shown in FIG. 7a, a spring member 40 comprises a substantially curvilinear central portion 40a in the form of a coil, and two substantially straight portions 40b extending therefrom at substantially 180° to each other. The second, shown in FIG. 7b is a spring member 42 comprising a substantially curvilinear portion 42a, comprising a coil as for the previous embodiment, with two substantially straight portions 42b extending therefrom at an angle of approximately 120° to each other. The third embodiment, shown in FIG. 7c, comprises a spring member 44 having a central substantially curvilinear portion 44a comprising a coil as previously, and two substantially straight portions 44b extending therefrom, but this time at approximately 0° to each other and substantially parallel. It will be appreciated that the spring members 40, 42 and 44 are shown unloaded, rather than as they would be after implantation with the patient in a normal rest position, by which time they would be loaded.

In each of the embodiments of spring member 40, 42 and 44 the substantially straight portions 40b, 42b and 44b are substantially coplanar, in that they are as close to coplanar as can be achieved when the substantially curvilinear portions 40a, 42a and 44a comprise coils.

The embodiments of assemblies according to the invention described and discussed thus far are for use between two adjacent vertebral bodies. Such embodiments can be used across adjacent motion segments, as illustrated in FIG. 8, if more than one motion segment requires stabilisation. In such cases the pedicle screw 20 located in the middle of the three vertebral bodies 14 has a modified fixation mechanism which can receive and secure the substantially straight portion of two spring members 18.

It is also possible for embodiments of assemblies according to the invention to be appropriate for use across more than a single motion segment. One such example, for use across two motion segments, is illustrated in FIG. 9 in which three vertebral bodies are shown referenced 12, 14 and 14'. A pedicle screw 20 is inserted into the upper most vertebral body 12, and into the lower most vertebral body 14'. A spring member 46, substantially of the form of the spring member 18 but of larger dimension, is secured between the two pedicle screws 20. Spring member 18 will be longer than embodiments previously described, and may be as long as 110 mm or 100 mm.

The exact design of spring members for use in a particular case will depend on a large number of factors. These will include the sizes of the vertebral bodies, the number of motion segments requiring stabilisation, and the particular condition being treated.

In the present specification "comprises" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An assembly for the stabilization of vertebral bodies of the spine, comprising:
    a pair of pedicle screws each having a threaded shaft with a tapering first end for introduction into a vertebral body and a head portion with a second end, wherein the head portion contains a slot;
    a spring member having first and second ends, substantially straight portions adjacent each end, and a substantially curvilinear central portion therebetween, wherein the substantially straight portions and the substantially curvilinear central portion are not in the same plane, wherein there is a sleeve located on each of the substantially straight portions, to effectively increase the external diameter of at least a part of each of the substantially straight portions, and wherein each sleeve fits within the slot of a corresponding head portion; and
    a pair of fixation mechanisms for securing the first and second ends of the spring member, by the sleeves, to the pair of pedicle screws, and
    characterized in that the substantially curvilinear central portion of the spring member is a coil.

2. An assembly according to claim 1, characterized in that the substantially curvilinear central portion of the spring member has a radius of curvature in the range 3 to 17 mm.

3. An assembly according to claim 2, characterized in that the substantially curvilinear central portion of the spring member has a radius of curvature in the range 5 to 15 mm.

4. An assembly according to any one of the preceding claims, characterized in that the substantially straight portions of the spring member are at angle to each other in the range 0 to 180°.

5. An assembly according to claim 4 characterized in the substantially straight portions of the spring member are at an angle to each other in the range 90 to 180 degrees.

6. An assembly according to claim 1 characterized in that the substantially straight portions of the spring member are parallel to each other.

7. An assembly according to claim 1 characterized in that the spring member is formed from one continuous wire.

8. An assembly according to claim 1 characterized in that the spring member has a diameter in the range 1 to 6 mm.

9. An assembly according to claim 1 characterized in that at least the parts of the substantially straight portions adjacent the ends of the spring member are of a greater cross-sectional area than that of the substantially central curvilinear portion.

10. An assembly according to claim 9 characterised in that the spring member has a diameter in the range 2 to 5 mm.

11. An assembly according to claim 1 characterized in that the sleeves have an external diameter in the range 5 mm to 8 mm.

12. An assembly according to claim 1 characterized in that the spring member is round in cross section.

13. An assembly according to claim 1 characterized in that the spring member is square or rectangular in cross section.

14. An assembly according to claim 1 characterized in that the spring member is formed from titanium or stainless steel.

15. An assembly according to claim 1 characterized in that the threaded shaft portions of the pedicle screws have lengths in the range 30 to 60 mm.

16. An assembly according to claim 15 characterised in that the threaded shaft portions of the pedicle screws have lengths in the range 35 to 55 mm.

17. An assembly according to claim 1 characterized in that the pedicle screws are formed from titanium.

18. An assembly according to claim 1 characterized in that the spring member is specifically adapted for stabilization of two adjacent vertebral bodies of the spine, that is one motion segment.

19. An assembly according to claim 18 characterised in that the spring member has a length in the range 20 to 65 mm.

20. An assembly according to claim 19 characterised in that the spring member has a length in the range 25 to 60 mm.

21. An assembly according to claim 1, characterized in that the spring member is specifically adapted for stabilization of three vertebral bodies of the spine, that is two motion segments.

22. An assembly according to claim 21 characterised in that the spring member has a length in the range 50-110 mm.

23. An assembly according to claim 22 characterised in that the spring member has a length in the range 60-100 mm.

* * * * *